United States Patent [19]

Tsuyumu et al.

[11] 4,335,236
[45] Jun. 15, 1982

[54] α-D-GALACTURONIDE DERIVATIVES

[75] Inventors: Shinji Tsuyumu; Keiichi Ota, both of Shizuoka, Japan

[73] Assignee: Otsuka Pharmaceutical Co., Ltd., Japan

[21] Appl. No.: 192,513

[22] PCT Filed: Jun. 19, 1979

[86] PCT No.: PCT/JP79/00155
§ 371 Date: Feb. 11, 1980
§ 102(e) Date: Feb. 11, 1980

[87] PCT Pub. No.: WO80/00082
PCT Pub. Date: Jan. 24, 1980

[30] Foreign Application Priority Data

Jun. 21, 1978 [JP] Japan ................................. 53/74093
Jun. 21, 1978 [JP] Japan ................................. 53/74094
Jul. 17, 1978 [JP] Japan ................................. 53/86071
Jul. 17, 1978 [JP] Japan ................................. 53/86072

[51] Int. Cl.³ ........................ C07H 15/04; C07H 5/10
[52] U.S. Cl. ................................. 536/18.2; 424/180; 424/283
[58] Field of Search .................... 536/4; 260/345.8 R, 260/345.7 R; 424/180, 283

[56] References Cited
U.S. PATENT DOCUMENTS 2,845,439 7/1958 Reiners ................................. 536/4
3,629,238 12/1971 Arasaki et al. ...................... 536/4

OTHER PUBLICATIONS

Heim et al., "Chem. Abst.", vol. 57, 1962, pp. 12,608(h)–12,609(a).
Llewellyn et al., "Chem. Abst.", vol. 76, 1972, p. 141,268z.
Tjan et al., "Chem. Abst.", vol. 81, 1974, p. 13719p.

Primary Examiner—Johnnie R. Brown
Attorney, Agent, or Firm—Larson and Taylor

[57] ABSTRACT

α-D-Galacturonide derivatives, salts thereof, and plant disease control agents containing the derivative or the salt as an active component. The derivatives are represented by the formula

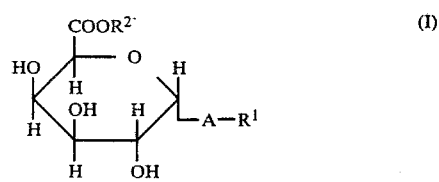

wherein $R^1$ is alkyl having 1 to 8 carbon atoms, alkenyl having 2 to 8 carbon atoms, cycloalkyl having 3 to 8 carbon atoms, aryl or a 5-membered or 6-membered unsaturated heterocyclic ring residue, $R^2$ is a hydrogen atom or methyl, A is an oxygen atom or sulfur atom, and the hydroxyl attached to the carbon atom at the 4-position of the galacturonide skeleton and the hydrogen atom attached to the carbon atom at the 5-position may be eliminated to form a double bond between the carbon atoms at the 4- and 5-positions.

The compounds represented by formula (I) are prepared by the processes represented by reaction schemes 1 to 3 as described below.

Reaction scheme 1

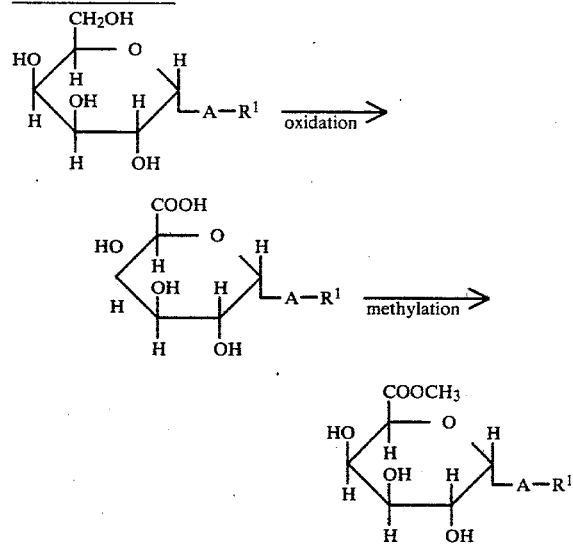

Reaction scheme 2

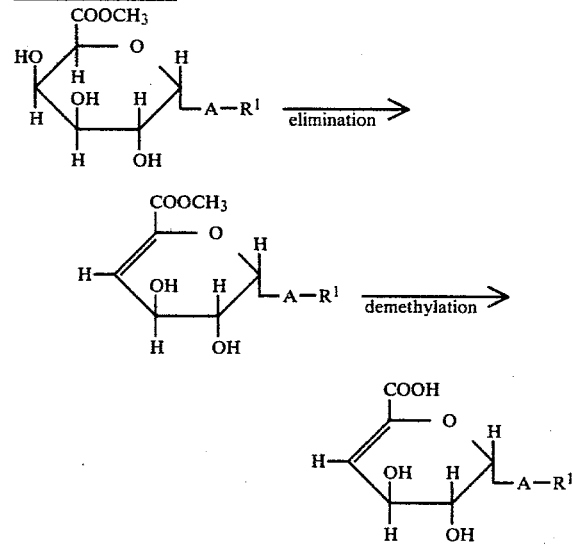

Reaction scheme 3

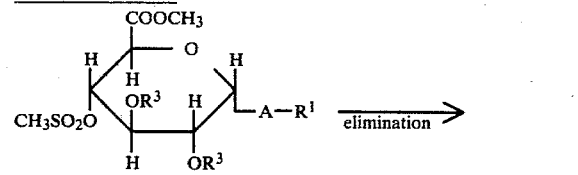

-continued
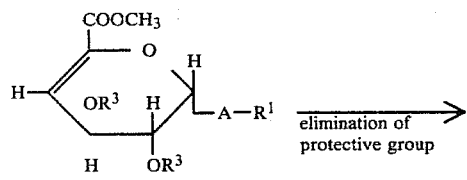
elimination of protective group →
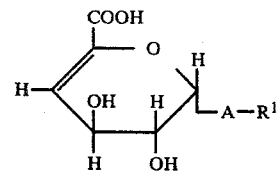
demethylation →
-continued
wherein $R^3$ is a protective group for hydroxyl group.
1 Claim, No Drawings

α-D-GALACTURONIDE DERIVATIVES

TECHNICAL FIELD

This invention relates to novel α-D-galacturonide derivatives and plant disease control agents containing the derivative as an active component.

DISCLOSURE OF INVENTION

The α-D-galacturonide derivatives of the invention are represented by the formula

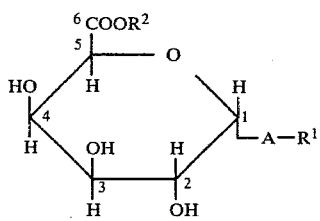

wherein $R^1$ is alkyl having 1 to 8 carbon atoms, alkenyl having 2 to 8 carbon atoms, cycloalkyl having 3 to 8 carbon atoms, aryl or a 5-membered or 6-membered unsaturated heterocyclic ring residue, $R^2$ is a hydrogen atom or methyl, A is an oxygen atom or sulfur atom, and the hydroxyl attached to the carbon atom at the 4-position of the galacturonide skeleton and the hydrogen atom attached to the carbon atom at the 5-position may be eliminated to form a double bond between the carbon atoms at the 4- and 5-positions. The invention provides such derivatives and salts thereof.

Exemplary of the alkyl having 1 to 8 carbon atoms and represented by $R^1$ in Formula (I) are methyl, ethyl, n-propyl, isopropyl, n-butyl, sec-butyl, isobutyl, tert-butyl, n-pentyl, isopentyl, n-hexyl, n-heptyl, n-octyl, etc. Examples of the alkenyl having 2 to 8 carbon atoms and represented by $R^1$ are vinyl, allyl, crotyl, 1-methylallyl, 2-methylallyl, 1,1-dimethylallyl, 2-pentenyl, 2-hexenyl, 4-hexenyl, 2-heptenyl, 2-octenyl, etc. Examples of the cycloalkyl having 3 to 8 carbon atoms and represented by $R^1$ are cyclopropyl, cyclobutyl, cyclopentyl, cyclohexyl, cyclooctyl, etc. The aryl represented by $R^1$ may be with or without a substituent. Exemplary of such a substituent is nitro. Examples of the aryl are phenyl, p-nitrophenyl, o-nitrophenyl, naphthyl, etc. The 5-membered or 6-membered unsaturated heterocyclic ring residue represented by $R^1$ means a 5-membered or 6-membered unsaturated heterocyclic ring having an oxygen atom, nitrogen atom or sulfur atom in the heterocyclic ring, examples thereof being furyl, thienyl, pyroyl, pyridyl, α-pyranyl, 4-methylumbelliferyl, etc.

The α-D-galacturonide derivatives represented by Formula (I) and salts thereof include the α-D-galacturonide derivatives represented by the formula

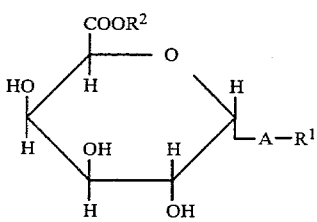

wherein $R^1$, $R^2$ and A are as defined above, and salts thereof, and the α-D-galacturonide derivatives represented by the formula

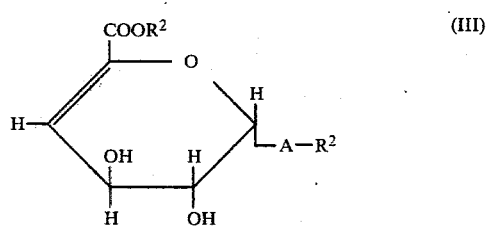

wherein $R^1$, $R^2$ and A are as defined above, and salts thereof.

The compounds of Formula (II) can be prepared, for example, by the process represented by Reaction Scheme 1 given below.

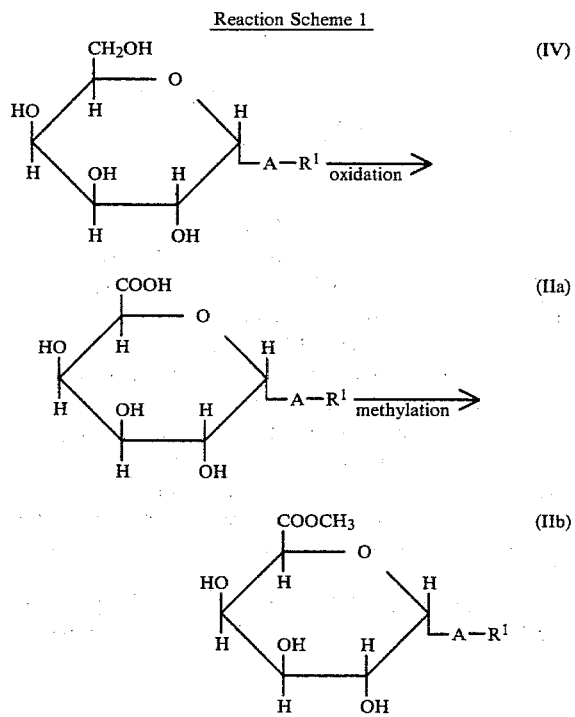

wherein $R^1$ and A are as defined above.

The compounds represented by Formula (IV) are known compounds. The compound represented by Formula (IIa) is prepared by oxidizing the compound of Formula (IV). The compound of Formula (IV) can be oxidized in the usual manner with use of platinum oxide, for example, as a catalyst.

The compound represented by Formula (IIb) is prepared by methylating the compound of Formula (IIa) thus obtained. The compound of Formula (IIa) can be easily methylated in the usual manner, for example, with use of hydrochloric acid-methanol mixture in absolute methanol.

The compounds of Formula (III) are prepared, for example, by the process represented by Reaction Scheme 2 given below.

Reaction Scheme 2

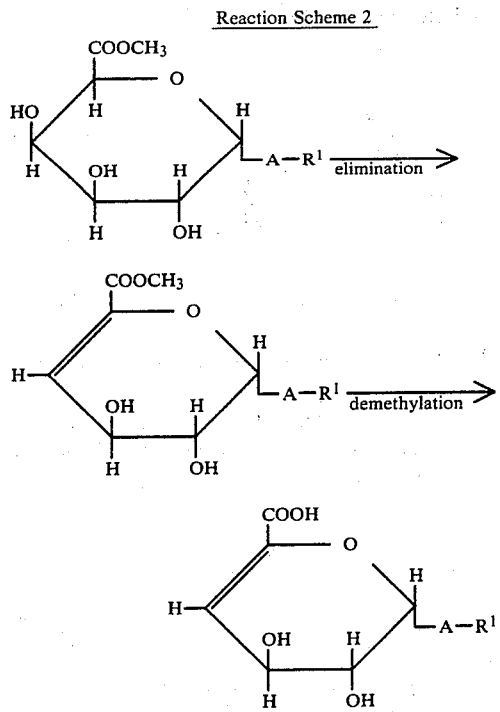

wherein $R^1$ and A are as defined above.

The compound represented by Formula (IIIa) is prepared by subjecting the compound of Formula (IIb) to an elimination reaction. The elimination reaction of the compound of Formula (IIb) can be conducted, for example, with use of a usual alkaline reagent, such as sodium ethylate, in absolute methanol.

The compound represented by Formula (IIIb) is prepared by demethylating the compound of Formula (IIIa) thus obtained. The demethylation of the compound of Formula (IIIa) can be easily carried out in the usual manner, for example, with use of an enzyme, such as methylesterase.

The compounds of Formula (III) can be prepared also by the process of Reaction Scheme 3 given below.

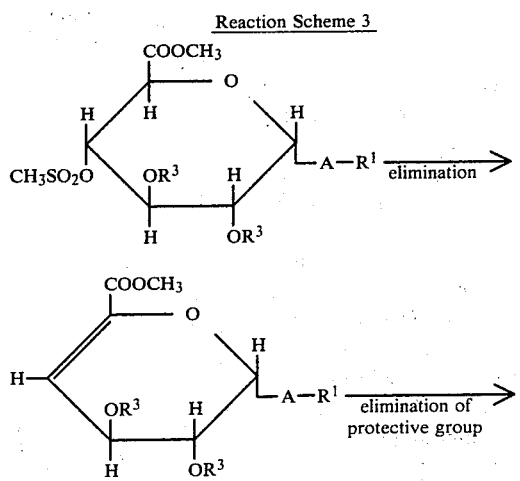

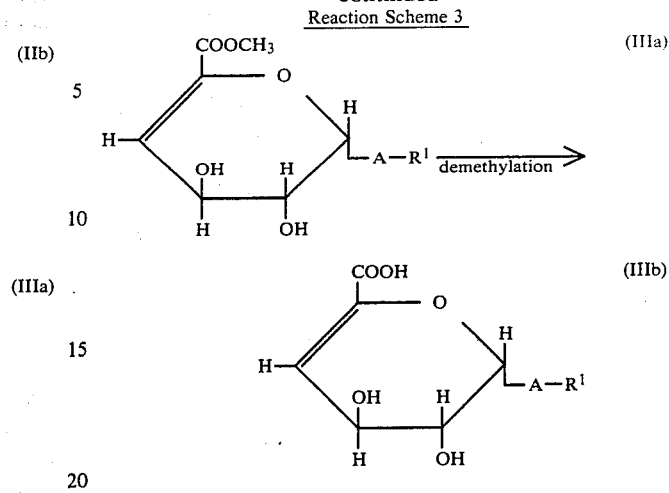

wherein $R^3$ is a benzyl ether residue, acetyl or like common protective group, and $R^1$ and A are as defined above.

The compound represented by Formula (V) is a known compound. The compound represented by Formula (VI) is prepared by subjecting the compound of Formula (V) to an elimination reaction. The elimination reaction of the compound of Formula (V) may be effected in the same manner as the elimination reaction of the compound (IIb).

The compound of Formula (IIIa) is prepared by eliminating the protective group $R^3$ from the compound of Formula (VI). The protective group can be eliminated by a known method.

The compound of Formula (IIIa) can be demethylated to the compound of Formula (IIIb) by the method already stated above.

The compound of the present invention thus obtained can be isolated from the reaction mixture and purified easily by a usual separating method, for example, by extraction, precipitation, recrystallization or chromatography.

Of the compounds of Formula (I) thus prepared, those in which $R^2$ is a hydrogen atom can be easily made into salts with use of basic compounds which are usually acceptable from the viewpoint of plant pharmacology. Such salts are also included in the compounds of this invention. Examples of useful basic compounds are hydroxides of alkali metals and alkaline earth metals, such as sodium, potassium, barium, magnesium, calcium, strontium, etc. The compound of Formula (I) can be converted to a corresponding salt by neutralizing the compound (I) with a basic compound of the above examples and precipitating the resulting salt with use of a hydrophilic solvent such as methanol, ethanol, dioxane, acetone or the like. The compound of Formula (I) can be converted to a strontium salt with use of strontium chloride, strontium nitrate or the like as the basic compound.

The compounds of Formula (I) and salts thereof are effective in controlling all the agricultural and horticultural plant pathogenic bacteria and fungi (including wood-decay fungi) having pectinases which decompose pectic substances. Examples of pectinases are pectic acid lyase, pectin lyase, polygalacturonase, pectin esterase, etc. Typical examples of such pathogens and plant diseases to be thereby caused are given below.

| Diseases | |
|---|---|
| Bacteria | |
| *Erwinia carotovora* | Soft rot |
| *Erwinia atroseptica* | Black leg |
| *Erwinia chrysanthemi* | Dwarf bacterial disease |
| *Pseudomonas solanacearum* | Bacterial wilt |
| *Pseudomonas Malginalis* | Sheath brown rot, Bacterial leaf spot |
| *Xanthomonas citri* | Canker |
| *Xanthomonas pisi* | Bacterial blight |
| *Xanthomonas malvacerum* | Angular leaf spot |
| *Xanthomonas campestris* | Black rot |
| Fungi | |
| *Rhizoctonia solani* | Sheath blight, Leaf rot, Stem rot |
| *Fusarium oxysporum* | Fusarium wilt, Stem rot, Wilt |
| *Colletotrichum falcatum* | Red rot |
| Fungi of Colletotrichum genus | Anphracnose |
| Fungi of Verticillium genus | Wilt |
| *Aspergillus niger* | Aspergillus rot |
| *Cochliobolus miyabeanus* | Brown spot |
| Fungi of Tricoderma genus | Tricoderma rot, Seedling blight, Wood decay |
| Fungi of Penicillium genus | Green mold |

The plant disease control agents containing the compound of Formula (I) or salt thereof as an active component are usable in the form of various preparations each suitable for a particular use. Examples of such preparations are liquid preparations such as solution, slurry, emulsion, wettable preparation, etc. and solid preparations such as particles, granules, pellets, etc. For application to soil, the plant disease control agents of this invention are used usually in the form of a solution, particles, granules, pellets or slurry. For application to seeds, fruits and plant bodies in the fields, the agents are applied by spraying, dusting, aerosol-spraying, injecting or immersing.

For the formulation of liquid preparations, water is most commonly used as a diluent, while for the formulation of emulsions or wettable preparations, it is advantageous to admix a spreader, such as "Kumiten", "Gramin", "Dain" (surface active agent containing alkylene oxide component), or "Mangra", "Rino" (coconut oil spreader containing lauryl diglycol ester) with the active component. The liquid preparations contain the active component preferably in a concentration of 3 to 6 g/liter. The spreader, if incorporated, is used preferably in a concentration of 0.01 to 0.03%.

Solid diluents useful for formulating solid preparations are vegetable fine particles such as soybean flour, wheat flour and wood flour, pyrophyllite, kaolinite group, montmorillonite group, attapulgite group, etc., which can be used singly or in admixture. The ratio of the active component to the solid diluent is preferably in the range of 1–3:99–97.

For the purpose of wood preservative, the plant disease control agents of this invention may be used in the same manner as above, singly or as admixed with a wax, paint or the like for building materials and furniture.

The plant disease control agents of the invention are of the novel type heretofore unknown. For example, when used for agricultural and horticultural applications, the plant disease control agents of the invention can be well absorbed by the plant body and can be retained therein for a prolonged period of time to act against pectinases and inhibit the activity of plant pathogens in the plant body. Thus, the agents are characterized by the effect of curing infected plants to healthy plants and the effect of protecting healthy plants from diseases.

Although few of the conventional agricultural and horticultural fungicides or bactericides are known to be effectively absorbable by plants and retainable therein for a prolonged period to exhibit sustained activity against fungi or bacteria, noteworthy as such is the fungicidal composition disclosed in Published Examined Japanese Patent Application No. 11319/1970. The composition contains an active component of the carbamate type which is incorporated therein merely in a reduced particle size so as to physically penetrate into the bodies of plants, as distinct from the agent of this invention which are positively absorbable by plants. Additionally the agricultural chemicals heretofore available always involve various pollution problems and require meticulous care for application, whereas the compounds of Formula (I) contained in the compositions of this invention as active components are all glycosides, so that the present compositions have the unique feature that they have low toxicity to man and animals and no phytotoxicity whatever. Accordingly the present compositions involve no likelihood of causing pollution that is usually attendant on the use of conventional agricultural chemicals and are therefore handleable or applicable with safety without necessitating any special care.

The compositions of this invention remain stable unless subjected to a strongly alkaline hot atmosphere, are readily soluble in water, and are satisfactorily spreadable when in the form of an aqueous solution. Thus the compositions have another advantage that an auxiliary agent need not always be incorporated therein.

The compositions of this invention have another advantage that they are in no way likely to give plant pathogens resistance thereto.

With such safety feature and stability, the present compositions are also suitable for preventing decay of the wood materials used for houses and furniture which are closely associated with daily life.

Since the compositions of this invention are substantially non-toxic to man and animals even if the active component is ingested by the living body, the compositions are usable for any food crops including vegetables, fruits and cereals to protect the crops from post-harvest diseases. Moreover the compositions are useful for preserving wood materials over a prolonged period of time against decay. These are unique features of the present compositions for use as agricultural chemicals.

The compositions of this invention are usable, for example, for agricultural and horticultural applications free of any limitations on the application time or site, or the type of the plant for which they are used. In the case of seed plants, for example, the compositions are applicable to the seeds and/or soil before sewing, or to the portions of the plant above and/or in the ground after germination. Thus they are applicable at any time in any site desired. Further in the case of transplantable plants, the compositions are applicable to seedlings, to the soil to which the seedlings are transplanted, or to grown-up trees. They are also applicable to the fruits on fruit trees. In this way, the compositions are usable in optionally selected fashion. In some cases it may be necessary to apply the compositions repeatedly several times.

The test results given below will indicate in greater detail the effectiveness of the compositions of this invention in preventing various agricultural and horticultural pathogens.

| Test bacteria | |
|---|---|
| *Erwinia carotovora* | (a) |
| *Xanthomonas campestris* | (b) |

Each of these two strains was incubated in a culture medium of a yeast extract, peptone and calcium chloride. A minimal liquid culture medium containing 2% glycerol as a carbon source was inoculated with one loopful of the culture, and the inoculum was incubated overnight. The culture was confirmed to be in the log-phase of the growth and used for the following test on the following day.

| Test compounds | |
|---|---|
| Ethyl-α-D-galacturonide | compound A |
| p-Nitrophenyl-α-D-galacturonide | compound B |
| Methyl ester of ethyl-α-D-$\Delta^{4,5}$-thiogalacturonide | compound C |
| Methyl ester of p-nitrophenyl-α-D-$\Delta^{4,5}$-galacturonide | compound D |

Induction inhibiting test

The suspension of each of the bacteria (a) and (b) was added, in equal amounts, to minimal culture media containing 1% pectinic acid (pH 8). The test compounds A to D were added to the media individually to a final concentration of 40 μg/ml. Two hours later, the bacteria were collected from each culture medium, washed and suspended in 0.05 M Tris-HCl buffer of pH 7.5, and the suspension was treated by an ultrasonic disintegrator for 30 seconds twice to obtain a bacterial extract. The activity of pectic acid lyase in the extract was determined by thiobarbituric acid method (see Weissbach, A. and Hurwitz, J., J. Biol. Chem. 234, 705–709 (1959). The protein concentration of the suspension was also measured by the Lowry method (see Lowry, O. H., Rosebrough, N.J., Farr, A. J. and Randall, R. J., J. Biol. Chem. 193, 265–275 (1951). The specific activity of enzyme is expressed by enzymatic unit (1 unit: amount of enzyme which produces 1 micromole of unsaturated digalacturonic acid per minute) per mg. of protein. The result is given in Table 1. The induction inhibiting effect was determined according to the numerical value of the specific enzyme activity. For comparison, the same procedure as above was repeated except that no test compound was added (control 1) and except that pectic acid and test compound were not used (control 2). The results are also listed in Table 1. In each case, the test was conducted twice, and the average value of the results is listed. When the induction of the enzyme was inhibited, the result is represented by "−," and when the enzyme was induced, by "+."

TABLE 1

| Test compound | Test bacteria (a) | | Test bacteria (b) | |
|---|---|---|---|---|
| | Specific enzyme activity | Induction of enzyme | Specific enzyme activity | Induction of enzyme |
| A | 2.2 | − | 1.5 | − |
| B | 2.1 | − | 1.5 | − |
| C | 2.2 | − | 1.5 | − |
| D | 2.1 | − | 1.7 | − |
| Control 1 | 16.5 | + | 12.2 | + |
| Control 2 | 2.2 | − | 1.5 | − |

Activity inhibition test

A 0.2 ml quantity of an enzyme substrate (a solution of 0.6% pectic acid and $10^{-4}$ M calcium chloride in 0.05 M Tris-HCl buffer of pH 8.0) and 0.1 ml (4 mg/ml) of the test compound were added to a 0.2 ml portion of the lysed bacterial extract of the control 1 used for the induction inhibiting test. In the same manner as in the induction inhibiting test, the activity of pectic acid lyase was assayed to determine the specific enzyme activity and evaluate the activity inhibiting effect. Table 2 shows the results. For comparison, the same procedure as above was repeated except that 0.1 ml of sterile distilled water was used in place of the test compound (control), with the results also listed in Table 2. In each case, the test was conducted twice, and the average value of the results is listed. When the activity of the enzyme was inhibited, the result is represented by "+," and when the activity was not inhibited, by "−."

TABLE 2

| Test compound | Test bacteria (a) | | Test bacterial (b) | |
|---|---|---|---|---|
| | Specific enzyme activity | Inhibition | Specific enzyme activity | Inhibition |
| A | 8.5 | + | 7.0 | + |
| B | 8.4 | + | 7.5 | + |
| C | 8.3 | + | 6.0 | + |
| D | 8.3 | + | 5.5 | + |
| Control | 16.1 | − | 12.2 | − |

Plant protection test

Test plant: Japanese radish

A commercial Japanese radish was cut to a thickness of about 1 cm, and the cut piece was placed into a Petri dish 8.5 cm in diameter and having filter paper placed therein as impregnated with sterile water.

A 0.1 ml of the suspension of the bacteria (a) or (b) ($1 \times 10^8$/ml) and 0.1 ml of a solution of the test compound (0.4 mg/ml) in sterile water were placed on the radish piece in the Petri dish and then spread with a sterile glass rod. When the Petri dish was incubated for 24 hours at 20° C., the treated radish piece did not rot. Another 0.1 ml of the same bacterial suspension was placed on the piece again. The test piece was thereafter checked for the degree of rot and for the rot preventing effect, with the results listed in Table 3 below. For comparison, the same procedure as above was repeated except that in place of the test compound, 0.1 ml of a solution of α-D-galactopyranoside (0.4 mg/ml) useful as the starting material for the synthesis of the compounds of this invention was placed on a radish piece, which was then incubated at 20° C. and checked for rot on the next day and seventh day (control 1). The same procedure as above was also repeated except that no test compound was placed on a radish piece, which was incubated at 20° C. and checked for rot on the next day and seventh day (control 2). These radish pieces were also checked for rot preventing effect, if any. The results are also given in Table 3. Rotted test pieces are represented by "+," and test pieces free of any rot by "−." The rot preventing effect, if achieved, is represented by "+," and otherwise, by "−."

TABLE 3

| Test compound | Rot | | | | Rot preventing effect | |
|---|---|---|---|---|---|---|
| | 1st day | | 7th day | | | |
| | (a) | (b) | (a) | (b) | (a) | (a) |
| A | − | − | − | − | + | + |
| B | − | − | − | − | + | + |

TABLE 3-continued

| Test | Rot | | | | Rot preventing effect | |
|---|---|---|---|---|---|---|
| | 1st day | | 7th day | | | |
| compound | (a) | (b) | (a) | (b) | (a) | (a) |
| C | − | − | − | − | + | + |
| D | − | − | − | − | + | + |
| Control 1 | + | + | + | + | − | − |
| Control 2 | + | + | + | + | − | − |

Cell toxicity test

The above-mentioned test bacteria were incubated in the same manner as in the induction inhibition test. Four hours latter, each of the cultures was checked for the optical density by a photoelectric colorimeter (with use of a filter 655 mμ in wavelength) to see the growth inhibiting effect. Tables 4 and 5 show the results. For comparison, the same incubating procedure was repeated except that no test compound was used (control), and the culture was checked for the optical density and for the growth inhibition. The results are also given in Tables 4 and 5. The optical density of each incubated culture medium was also measured at the start of incubation in the same manner as above. The results are also listed in Tables 4 and 5. The presence of growth inhibition is represented by "+," and the absence of growth inhibition by "−."

TABLE 4

| | Optical density | | Inhibition of growth | |
|---|---|---|---|---|
| | (a) | (b) | (a) | (b) |
| At start of incubation | 0.112 | 0.110 | | |
| Compound A | 0.263 | 0.264 | − | − |
| Compound B | 0.263 | 0.264 | − | − |
| Control | 0.250 | 0.251 | − | − |

TABLE 5

| | Optical density | | Inhibition of growth | |
|---|---|---|---|---|
| | (a) | (b) | (a) | (b) |
| At start of incubation | 0.130 | 0.150 | | |
| Compound C | 0.285 | 0.295 | − | − |
| Compound D | 0.280 | 0.290 | − | − |
| Control | 0.280 | 0.260 | − | − |

Given below are examples for the production of compounds of this invention and examples of preparations.

EXAMPLE 1

Into distilled water was placed platinum oxide (50 ml/g), and the mixture was continuously stirred by a magnetic stirrer for about 30 minutes in a closed flask with its interior atmosphere replaced by hydrogen gas to obtain platinum black. The platinum black was washed with distilled water and admixed with distilled water containing ethyl-α-D-thiogalactopyranoside (J.O.C., 24, 1529 (1959)), in an amount of 1.7 times the quantity of the platinum black. The mixture was continuously stirred in an oxygen stream at a pH of 8 to 9 at 70° C. for about 1 hour and then filtered. The filtrate was concentrated in a vacuum to about 1/10 the quantity thereof and precipitated with use of ethanol about 4 times the quantity of the concentrate. The precipitate was dissolved in a small amount of distilled water again and adjusted to a reduced pH of 2.2 with a 10% solution of sulfuric acid. After repeating separation with ethyl oxide solvent, the acid was removed from the resulting product, and water was removed therefrom with sodium sulfate. With addition of a small amount of ethyl acetate, the product was separated out at 4° C. and dried by suction, giving ethyl-α-D-thiogalacturonide (m.p. 131° C., characteristic infrared absorption bands ($cm^{-1}$): 3490, 1720) in a yield of 55%.

EXAMPLE 2

In the same manner as in Example 1 except that p-nitrophenyl-α-D-galactopyranoside was used in place of ethyl-α-D-thiogalactopyranoside, p-nitrophenyl-α-D-galacturonide (m.p. 149° C., characteristic infrared absorption bands ($cm^{-1}$): 3500, 1720) was obtained in a yield of 27.6%.

EXAMPLE 3

In the same manner as in Example 1 except that o-nitrophenyl-α-D-galactopyranoside was used in place of ethyl-α-D-thiogalactopyranoside, o-nitrophenyl-α-D-galacturonide (m.p. 142° C., characteristic infrared absorption bands ($cm^{-1}$): 3480, 1730, producing a characteristic yellow color when heated with a strong alkali) was obtained in a yield of 25%.

EXAMPLE 4

In the same manner as in Example 1 except that cyclopentyl-α-D-galactopyranoside was used in place of ethyl-α-D-thiogalactopyranoside, cyclopentyl-α-D-galacturonide was obtained.

EXAMPLE 5

Allyl-α-D-galacturonide was prepared in the same manner as in Example 1 except that allyl-α-D-galactopyranoside was used in place of ethyl-α-D-thiogalactopyranoside.

EXAMPLE 6

(2-Thienyl)-α-D-galacturonide was prepared in the same manner as in Example 1 except that (2-thienyl)-α-D-galactopyranoside was used in place of ethyl-α-D-thiogalactopyranoside.

EXAMPLE 7

The ethyl-α-D-thiogalacturonide prepared in Example 1 was dissolved in absoluted methanol (in a ratio of 1 mole of the former to 20 moles of the latter). A mixture of 1 N hydrochloric acid and methanol was slowly added to the solution at room temperature, and the mixture was allowed to stand for 2 to 3 hours, then neutralized with AMBERLITE IR 120 of the OH type and filtered. The filtrate was concentrated. The concentrate was added to cold methanol, and the mixture was filtered. With addition of sodium methoxide, the filtrate was refluxed, giving methyl ester of ethyl-α-D-$\Delta^{4,5}$-thiogalacturonide (ultraviolet absorption at 235 mμ, thiobarbituric reaction: positive, characteristic infrared absorption bands ($cm^{-1}$): 3490, 1720, 1650) in a yield of 25%.

EXAMPLE 8

The procedure of Example 7 was repeated except that the p-nitrophenyl-α-D-galacturonide obtained in Example 2 was used, affording methyl ester of p-nitrophenyl-α-D-$\Delta^{4,5}$-galacturonide (ultraviolet absorption at 235 mμ, thiobarbituric reaction: positive, characteristic infrared absorption bands ($cm^{-1}$): 3480, 1730, 1660) in a yield of 23.5%.

EXAMPLE 9

The procedure of Example 7 was repeated except that the o-nitrophenyl-α-D-galacturonide obtained in Example 3 was used, affording methyl ester of o-nitrophenyl-α-D-$\Delta^{4,5}$-galacturonide (ultraviolet absorption at 235 mμ, thiobarbituric reaction: positive, characteristic infrared absorption bands (cm$^{-1}$): 3480, 1730, 1660) in a yield of 26%.

PREPARATION EXAMPLE 1

Ethyl-α-D-thiogalacturonide (40 g) was dissolved in 10 liters of tap water with stirring.

PREPARATION EXAMPLE 2

Calcium ethyl-α-D-thiogalacturonide (50 g), 300 g (solids weight) of "Kumiten" (Kumiai Chem. Co., Ltd.) and 10 liters of water were mixed together to obtain a uniform dispersion.

PREPARATION EXAMPLE 3

Sodium o-nitrophenyl-α-D-galacturonide (200 g) and 9.8 kg of a mixture of wood flour and pyrophyllite were mixed together to obtain a powder.

PREPARATION EXAMPLE 4

Sodium ethyl-α-D-thiogalacturonide (300 g) was mixed with 9.7 kg of montmorillonite, and the mixture was kneaded with water and made into pellets with a pelletizer.

PREPARATION EXAMPLE 5 p-Nitrophenyl-α-D-galacturonide (30 g) was dissolved in 10 liters of tap water with stirring.

PREPARATION EXAMPLE 6

Methyl ester of ethyl-α-D-$\Delta^{4,5}$-thiogalacturonide (60 g) was dissolved in 10 liters of tap water with stirring.

PREPARATION EXAMPLE 7

Ethyl-α-D-$\Delta^{4,5}$-thiogalacturonide (40 g) was dissolved in 10 liters of tap water with stirring.

PREPARATION EXAMPLE 8

Potassium ethyl-α-D-$\Delta^{4,5}$-thiogalacturonide (300 g) and 9.7 kg of mixture of fine soybean flour and wheat flour were mixed together, and the mixture was kneaded with addition of water and made into a solid preparation in the form of fine particles.

PREPARATION EXAMPLE 9

Methyl ester of p-nitrophenyl-α-D-$\Delta^{4,5}$-galacturonide (50 g) was dissolved in 10 liters of tap water, and 250 g (solids weight) of "Gramin" was added to the solution to obtain a homogeneous preparation.

PREPARATION EXAMPLE 10

Sodium o-nitrophenyl-α-D-$\Delta^{4,5}$-galacturonide (400 g) was mixed with 9.6 kg of montmorillonite, and the mixture was kneaded with addition of water and made into pellets with a pelletizer.

PREPARATION EXAMPLE 11 p-Nitrophenyl-α-D-$\Delta^{4,5}$-galacturonide (60 g) was dissolved in 10 liters of tap water with stirring.

INDUSTRIAL APPLICABILITY

The novel α-D-galacturonide derivatives and plant disease preventing agents of this invention are useful for preventing plant diseases and are fully useful for industrial applications.

We claim:

1. An α-D-galacturonide derivative represented by the formula

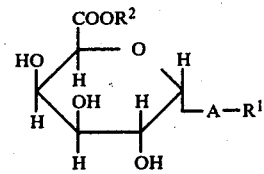

wherein R$^1$ is alkyl having 1 to 8 carbon atoms, alkenyl having 2 to 8 carbon atoms, cycloalkyl having 3 to 8 carbon atoms, phenyl, P-nitrophenyl, O-nitrophenyl, naphthyl, furyl, thienyl, pyrol, pyridyl, α-pyranyl and 4-methyl-umbellifenyl, R$^2$ is a hydrogen atom or methyl, A is an oxygen atom or sulfur atom with the proviso that when R$^1$ is alkyl having 1 to 8 carbon atoms, A is a sulfur atom, and the hydroxyl attached to the carbon atom at the 4-position of the galacturonide skeleton and the hydrogen atom attached to the carbon atom at the 5-position may be eliminated to form a double bond between the carbon atoms at the 4- and 5-positions.

* * * * *